(12) United States Patent
Mottola et al.

(10) Patent No.: US 11,160,951 B2
(45) Date of Patent: Nov. 2, 2021

(54) SYSTEMS AND METHOD FOR REDUCING MEDICAL COMPONENT DEGRADATION

(71) Applicant: Merit Medical Systems, Inc., South Jordan, UT (US)

(72) Inventors: Jim Mottola, West Jordan, UT (US); Steven Weir, Sandy, UT (US); Richard A. Brotherton, Park City, UT (US); Elena Agafonova, Park City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 84 days.

(21) Appl. No.: 16/193,625

(22) Filed: Nov. 16, 2018

(65) Prior Publication Data

US 2019/0151606 A1    May 23, 2019

Related U.S. Application Data

(60) Provisional application No. 62/587,617, filed on Nov. 17, 2017.

(51) Int. Cl.
| | |
|---|---|
| *B65D 83/10* | (2006.01) |
| *A61L 15/00* | (2006.01) |
| *A61M 25/00* | (2006.01) |
| *B65B 55/02* | (2006.01) |
| *A61L 2/26* | (2006.01) |
| *A61L 2/20* | (2006.01) |
| *A61M 25/01* | (2006.01) |
| *B65B 55/10* | (2006.01) |

(52) U.S. Cl.
CPC ........... *A61M 25/002* (2013.01); *A61L 2/206* (2013.01); *A61L 2/208* (2013.01); *A61L 2/26* (2013.01); *B65B 55/02* (2013.01); *A61L 2202/181* (2013.01); *A61L 2202/24* (2013.01); *A61M 25/0111* (2013.01); *B65B 55/10* (2013.01)

(58) Field of Classification Search
CPC .. A61M 25/002; A61M 25/0111; A61L 2/206; A61L 2/208; A61L 2/26; A61L 2202/181; A61L 2202/24; B65D 81/245
USPC .......................... 206/363, 364, 438, 570, 571
See application file for complete search history.

(56) References Cited

U.S. PATENT DOCUMENTS

| | | | | |
|---|---|---|---|---|
| 4,603,538 A | * | 8/1986 | Shave ...................... | A61L 2/206 53/425 |
| 5,131,537 A | * | 7/1992 | Gonzalez ............ | A61M 25/002 206/364 |

(Continued)

FOREIGN PATENT DOCUMENTS

WO    2005073091    8/2005

OTHER PUBLICATIONS

International Search Report and Written Opinion dated Mar. 5, 2019 for PCT/US2018/061631.
European Search Report dated Jul. 19, 2021 for EP18877928.4.

*Primary Examiner* — Luan K Bui
(74) *Attorney, Agent, or Firm* — Stoel Rives LLP (57) ABSTRACT

A packaging system and method for reducing or eliminating exposure of medical devices to whole-room disinfecting gases and vapors are disclosed. In some embodiments, the packaging system and method may comprise a diffusion inhibitor member configured as an open-ended bag. In some embodiments, the diffusion inhibitor member comprises polyethylene or polypropylene.

8 Claims, 4 Drawing Sheets

(56) References Cited

U.S. PATENT DOCUMENTS

| | | | |
|---|---|---|---|
| 5,163,554 A * | 11/1992 | Lampropoulos | A61M 25/002 206/363 |
| 5,226,530 A * | 7/1993 | Golden | A61M 25/002 206/210 |
| 5,447,231 A * | 9/1995 | Kastenhofer | A61B 1/00144 206/363 |
| 5,497,601 A * | 3/1996 | Gonzalez | A61M 25/002 206/364 |
| 5,501,341 A * | 3/1996 | Van Es | A61M 25/002 206/364 |
| 7,331,463 B2 | 2/2008 | Hickey | |
| 2005/0268573 A1 | 2/2005 | Yan | |
| 2005/0092636 A1 * | 5/2005 | Su-Syin | B65B 55/18 206/363 |
| 2005/0109648 A1 * | 5/2005 | Kerzman | A61M 25/0111 206/364 |
| 2007/0107381 A1 | 5/2007 | Vanhamel et al. | |
| 2008/0116106 A1 | 5/2008 | Lampropoulos et al. | |
| 2012/0124943 A1 | 5/2012 | Nakamura et al. | |

\* cited by examiner

| Test Sample Comparison | P-Value |
|---|---|
| No VHP Exposure vs 10x VHP Exposure | 0.000 |
| Diffusion Inhibitor + 10x VHP Exposure vs No VHP Exposure | 0.842 |
| Long Diffusion Inhibitor + 10x VHP Exposure vs Short Diffussion Inhibitor + 10x VHP Exposure | 0.785 |

*FIG. 5*

SYSTEMS AND METHOD FOR REDUCING MEDICAL COMPONENT DEGRADATION

RELATED APPLICATIONS

This application claims priority to U.S. Provisional Application No. 62/587,617, filed on Nov. 17, 2017 and titled, "Systems and Method for Reducing Medical Component Degradation," which is hereby incorporated by reference in its entirety.

TECHNICAL FIELD

The field of the present disclosure relates generally to medical devices. In some embodiments, the present disclosure relates to storage packages which prevent or reduce degradation of polymer medical device components such as when exposed to whole-room disinfecting vapors or gases. In some embodiments, the present disclosure relates to reducing or preventing the degradation of polymer catheter tips.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Prevention of hospital acquired infections (HAI) is a focus of certain hospital resources. HAI results in morbidities and mortality to hospitalized patients that significantly impact the lives of patients and increase the cost of healthcare. Types of HAIs include pneumonia, gastrointestinal illness, urinary tract infections, blood stream infections, and surgical site infections.

Decontamination of surgical rooms has been found to be an effective method of reducing surgical site infections. Surgery rooms with associated equipment and supplies are decontaminated using technologies such as Vaporized Hydrogen Peroxide (VHP), formaldehyde gas, and chlorine dioxide gas. VHP is pumped into a surgical room and allowed to dwell for a period of time. During the dwell time the VHP vapor, in a 'wet' process, reaches dew point and condensates on exposed surfaces of floors, walls, equipment and supplies. In a 'dry' process (VHP vapor concentration is below the dew point) the VHP does not condense on surfaces but does make contact with the surfaces. VHP oxidizes the cell wall of bio-contaminants, including drug resistant microbes such as Methicillin-resistant Staphylococcus aureus (MRSA) and Vancomycin-resistant *Enterococcus* (VRE). Following the dwell time, VHP is evacuated from the room leaving a disinfected room with a reduced risk of exposing a patient to any virulent bio-contaminants.

VHP is an effective tool to decontaminate or disinfect a surgical room. However, exposure to VHP may cause degradation of polymer based medical devices that may be stored in the surgical room. These medical devices may be diagnostic or therapeutic vascular catheters packaged in porous materials. The VHP may penetrate the porous material and interact with the surface of the medical device. Hydrogen peroxide is a strong oxidizing agent. The hydrogen peroxide may cause degradation of the polymer of the catheter from the outside surface. Repeated exposure to VHP may result in a catheter material that is brittle and weak. Such catheters may fracture or catheter tips may break off in a patient when the catheter is used for a procedure. In some such instances, a portion of the catheter or tip may need to be retrieved from the vasculature of a patient.

As further detailed below, a packaging component may be configured to provide a diffusion inhibitor member to reduce exposure of a portion of a polymeric medical device to a decontaminating vapor or gas. Some packaging components and methods may be configured to reduce or prevent polymer component degradation when exposed to whole-room disinfecting techniques. Some such techniques may include whole-room disinfection with VHP, formaldehyde gas, chlorine dioxide gas, or any other gas or vaporized agent suitable to perform whole-room decontamination.

In the following detailed description, reference is made to the accompanying drawings which form a part hereof and in which are shown, by way of illustration, specific embodiments of the disclosure that may be practiced. These embodiments are described in sufficient detail to enable those of ordinary skill in the art to practice the present disclosure, and it is to be understood that other embodiments may be utilized, and that structural, and logical changes may be made within the scope of the disclosure. From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In this description, specific implementations are shown and described only as examples and should not be construed as the only way to implement the present disclosure unless specified otherwise herein. It will be readily apparent to one of ordinary skill in the art that the various embodiments of the present disclosure may be practiced with numerous other vascular access solutions. The devices and methods described herein could be useful in a number of environments that employ packaging any polymer component, such as medical device components made of various polymers.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

While the disclosure is susceptible to various modifications and implementation in alternative forms, specific embodiments have been shown by way of non-limiting example in the drawings and have been described in detail herein. However, it should be understood that the disclosure is not intended to be limited to the particular forms disclosed. Rather, the disclosure includes all modifications, equivalents, and alternatives falling within the scope of the disclosure as defined by the following appended claims and their legal equivalents.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method, but are merely idealized representations employed to more clearly and fully depict the present invention defined by the claims below.

Figure 1:
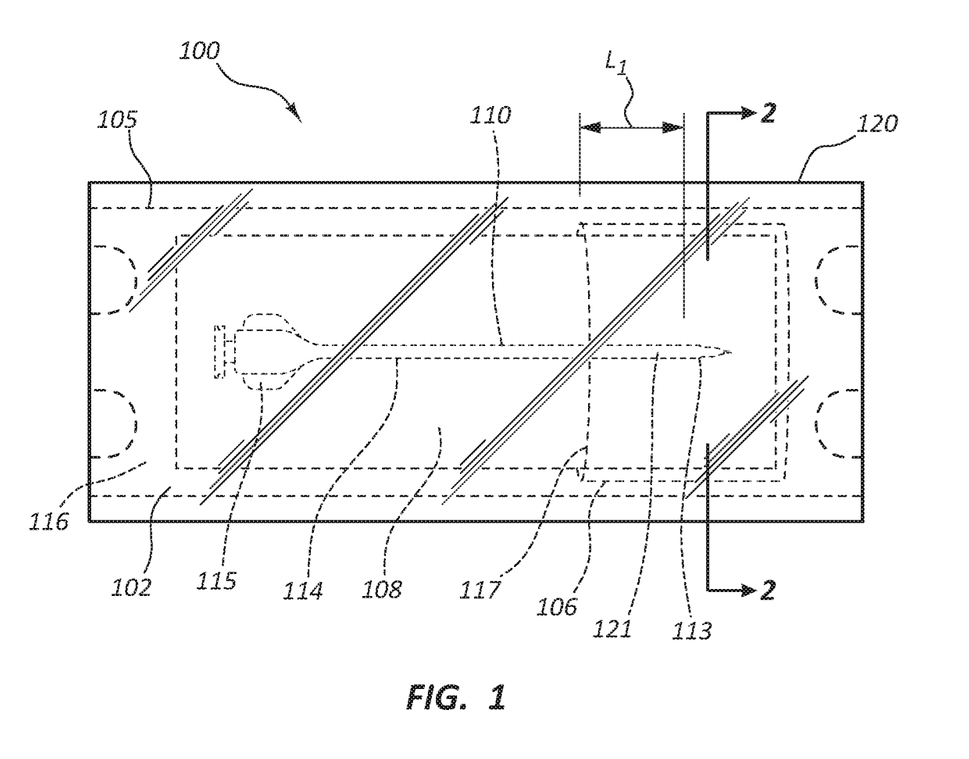
FIG. 1 is a top view of certain components of a packaging system.
Figure 2:
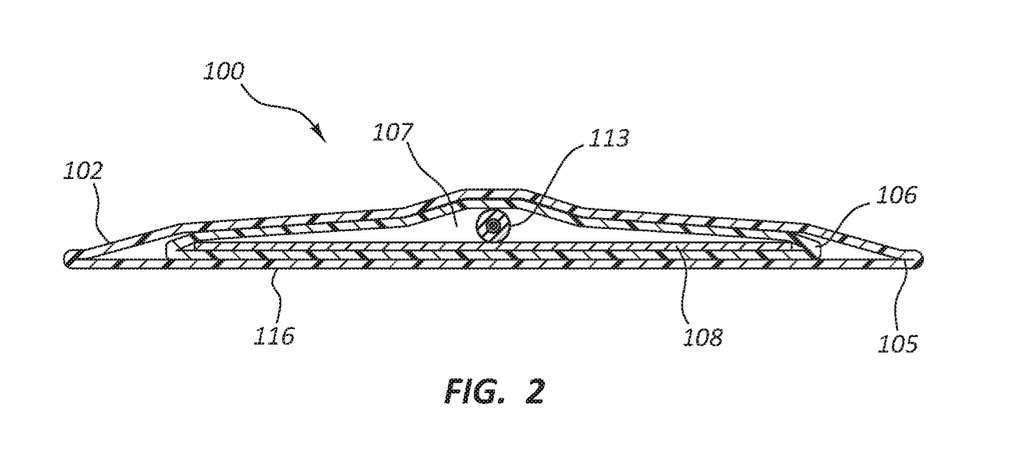
FIG. 2 is a cross-section view of certain components of the packaging system of FIG. 1 through section line 2.
Figure 3A:
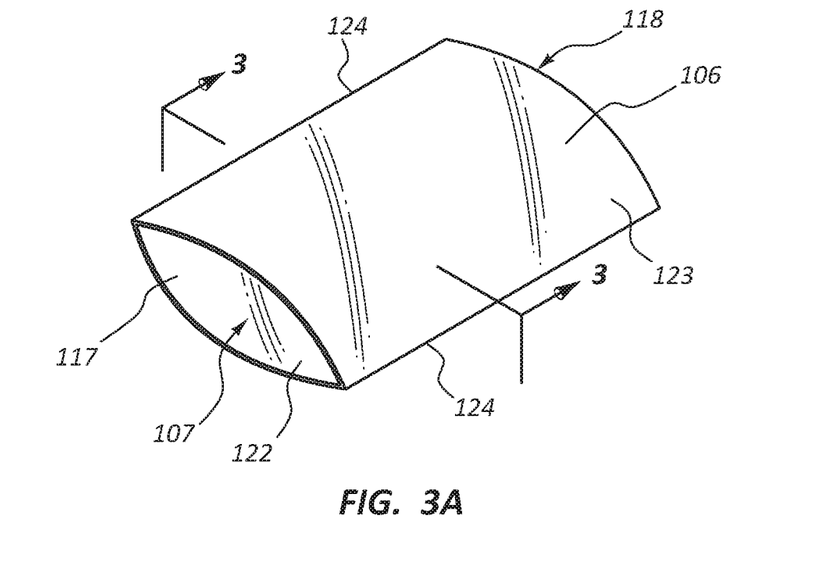
FIG. 3A is a perspective view of a diffusion inhibitor member.
Figures 3B, 3C:
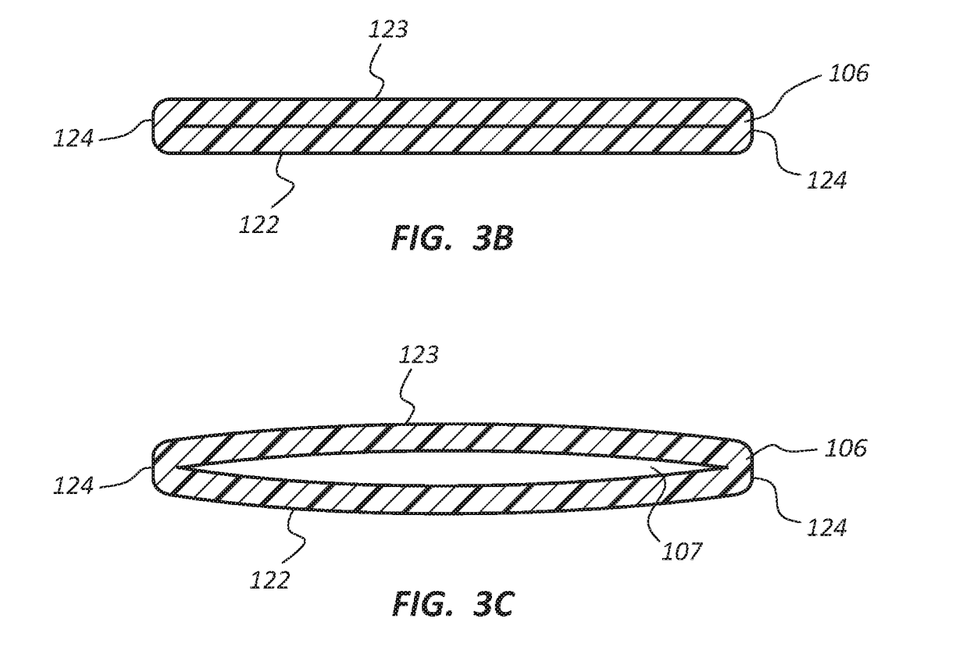
FIG. 3B is a cross-section view of the diffusion inhibitor member of FIG. 3A through section line 3, in a first configuration.
FIG. 3C is a cross-section view of the diffusion inhibitor member of FIG. 3A through section line 3, in a second configuration.

FIGS. 1-3 depict various views of individual components of a packaging system 100. FIG. 1 depicts a top view of the packaging system 100. Section line 2 of FIG. 1 indicates the line at which the cross-section depicted in FIG. 2 is taken. The packaging system 100 comprises a primary package 120, a support member 108, and a diffusion inhibitor member 106.

In some embodiments, the packaging system 100 is configured to contain a medical device 110, such as a vascular catheter. The medical device 110 comprises an elongate shaft 114, a connector 115 coupled to the proximal end of the elongate shaft 114, and a catheter tip 113 coupled to a distal end of the elongate shaft 114. The components of the medical device 110 may be formed from any suitable polymer or combination of polymers, such as polyethers, polyesters, nylon, polyether block amide, PEBAX®, polyurethane, etc. The elongate shaft 114 may comprise a stainless steel metal braid configured to increase physical characteristics of the elongate shaft 114, such as burst strength, kink resistance, rotatability, etc. A length of the elongate shaft 114 may range from 20 cm to 150 cm, including 30 cm to 125 cm. A diameter of the elongate shaft 114 may range from two French to eight French, including four French to five French. Other sizes and configurations of medical devices and catheters are within the scope of this disclosure.

The catheter tip 113 may be formed of a material or otherwise configured such that the catheter tip 113 is softer and/or more flexible than the elongate shaft 114. In some embodiments, the catheter tip 113 may be configured to minimize trauma when contacting a patient's vasculature and may not comprise a braid. The catheter tip 113 may be tapered at a distal end to facilitate passage of the medical device 110 through the vasculature of the patient.

The catheter tip 113 may also comprise a filler to increase radiopacity of the catheter tip 113. The increased radiopacity may allow the catheter tip 113 to be more easily identified within the vasculature of the patient using X-ray or fluoroscopy. The catheter tip 113 may be loaded with up to 80% by weight of any suitable radiopacifier filler, such as tungsten, tungsten carbide, barium sulfate, bismuth trioxide, bismuth subcarbonate, etc. Other fillers, such as color pigments, colarants, stabilizers, UV inhibitors, etc. may be incorporated into the material of the catheter tip 113. In some embodiments, the elongate shaft 114 and the catheter tip 113 may be coated with a hydrophilic coating configured to facilitate passage of the medical device 110 through the patient's vasculature. In some embodiments, the catheter tip 113 is coupled to the elongate shaft 114 utilizing heat and pressure. The elongate shaft 114 and the catheter tip 113 may be placed over a mandrel. The elongate shaft 114, catheter tip 113 and mandrel may then be inserted into a die that is heated by induction energy, such as radiofrequency energy. Application of a longitudinal force to the elongate shaft 114 and the catheter tip 113 as the materials of the elongate shaft 114 and the catheter tip 113 soften and melt may be utilized to bond the components. Furthermore, during this heating and application of force, a weld line 121 between the distal end of the elongate shaft 114 and a proximal end of the catheter tip 113 may be formed and the tapered shape of the distal end of the catheter tip 113 may be formed. The die is then cooled and the coupled elongate shaft 114 and catheter tip 113 are removed from the die. In other embodiments, other suitable techniques to couple the elongate shaft 114 and catheter tip 113 together may be used, such as gluing, over molding, laser welding, solvent bonding, etc. The catheter tip 113 may be formed as a straight extension of the elongate shaft 114. In other embodiments, the catheter tip 113 may be formed in any suitable two dimensional or three dimensional shape suitable to accomplish an intended intravascular procedure.

In the illustrated embodiment, the connector 115 is coupled to the proximal end of the elongate shaft 114. The connector 115 may comprise a female type Luer fitting configured to be coupled with male Luer fittings of medical components needed to accomplish a diagnostic or therapeutic procedure. The connector 115 may comprise wings to facilitate coupling and decoupling of the medical components. Various other connectors are within the scope of this disclosure.

With continued reference to FIGS. 1 and 2, the primary package 120 comprises a breathable portion, such as breathable layer 116 and a second layer, such as clear film layer 102. The breathable layer 116 is configured to allow passage of a sterilizing gas into the primary package 120 and to prevent passage of microbes into the primary package 120. For example, the breathable layer 116 may be configured to allow passage of ethylene oxide gas, across a wall of the breathable layer into the primary package 120 such that the medical device 110 may be sterilized by the ethylene oxide gas. The breathable layer 116 may comprise any suitable porous material, such as Tyvek®, paper, etc. A surface of the breathable layer 116 may be coated with a thermal or pressure sensitive adhesive such that the clear film layer 102 can be coupled to the breathable layer 116. The clear film layer 102 may be sealed to the breathable layer 116 around the edges of the primary package 120 using heat and pressure or just pressure. A seal 105 may be configured to be peelable such that the primary package 120 can be opened by a healthcare worker to access the medical device 110. The breathable layer 116 is shown to extend from a first end to a second end of the primary package 120. In other embodiments, the breathable layer 116 may comprise only a portion of the primary package 120. For example, the breathable layer 116 may be disposed adjacent one end of the primary package 120. In another embodiment, the breathable layer 116 may be a circular patch disposed along a length of the primary package 120. The clear film layer 102 may be formed from any suitable clear polymer, such as high density polyethylene, linear low density polyethylene, polypropylene, polyester, etc. A label may be adhered to the clear film layer 102 indicating the type of medical device 110 contained within the primary package 120.

In the illustrated embodiment, the support member 108 is disposed within the primary package 120 between the breathable layer 116 and the clear film layer 102. The medical device 110 may be coupled to the support member 108 using any suitable technique such that the shape of the medical device 110 is maintained within the primary package 120. Coupling techniques may include tabs, wires, adhesive, tape, plastic sleeves, etc. The support member 108 may be formed of any suitable non-particulate generating material, such as paper, cardboard, card stock, polymer sheet, thermoformed polymer sheet, etc.

The diffusion inhibitor member 106 is configured to protect or shield the medical device 110 from exposure to VHP or other whole-room disinfecting vapors or gases while still allowing for sterilization of the medical device 110 disposed within the primary package 120 with ethylene oxide gas. The diffusion inhibitor member 106 is disposed over an end of the support member 108, the catheter tip 113, and a portion of the elongate shaft 114. The diffusion inhibitor member 106 is configured to cover a portion $L_1$ of the elongate shaft 114. In other embodiments, the diffusion inhibitor member 106 may be configured to cover from one inch to a full length of the elongate shaft 114, including from one inch to seven inches of the elongate shaft 114.

Referring to FIGS. 3A-3C, the diffusion inhibitor member 106 is configured as a bag or sleeve having a first wall 122, a second wall 123, an open end 117, a closed end 118, and closed lateral sides 124 such that an internal cavity 107 is created. In some embodiments, the diffusion inhibitor member 106 may be configured as a tube comprising at least one open end. In other embodiments, the diffusion inhibitor member may be open at a proximal and/or a distal end. The diffusion inhibitor member 106 may be formed from any suitable substantially non-porous, material, such as polyethylene, polypropylene, polyesters, foil laminations, paper/polyethylene laminations, vinyl (PVC), nylon, etc. The walls 122, 123 of the diffusion inhibitor member 106 may have a thickness ranging from 0.001 inch to 0.005 inch, including 0.002 inch to 0.003 inch. The thickness of the walls 122, 123 is configured to allow for easily sliding the diffusion inhibitor member 106 over the support member 108 and the medical device 110 while inhibiting diffusion of VHP or any other whole-room disinfecting vapor or gas within the internal cavity 107.

In other embodiments, the diffusion inhibitor member 106 may be configured as bag sized to be disposed over just the medical device 110. The diffusion inhibitor member 106 may also be configured to conform to a shape of the catheter tip 113 such that the shape is maintained by the diffusion inhibitor member 106.

Figure 4:
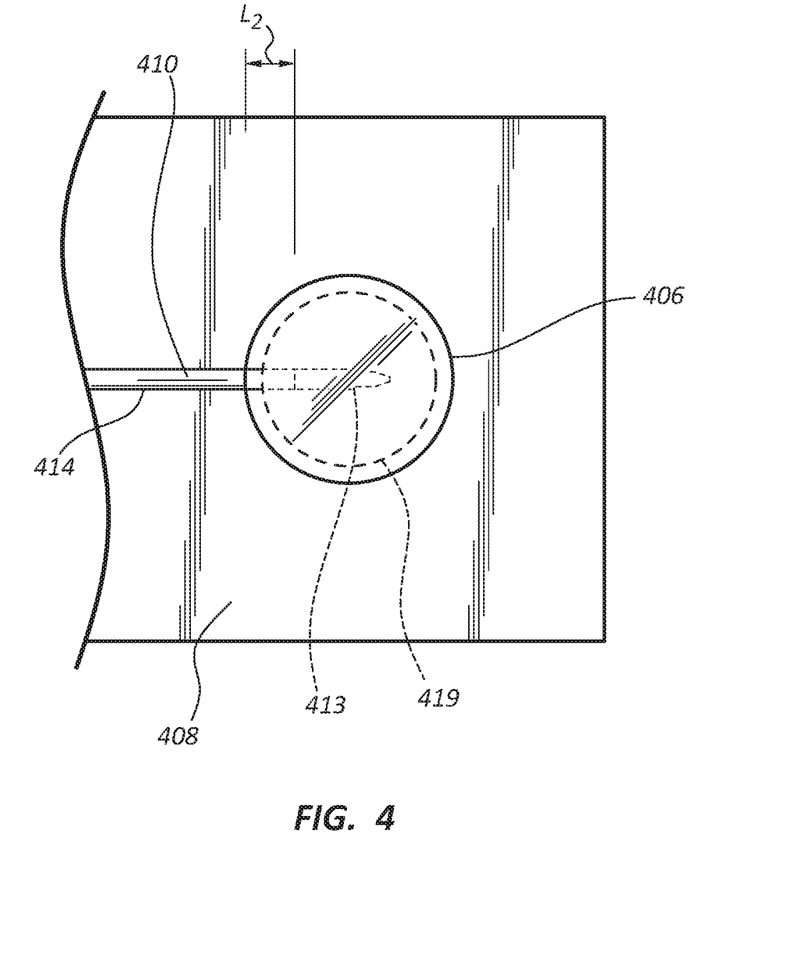
FIG. 4 is a top view of certain components of a packaging system.

FIG. 4 depicts an alternative embodiment of a diffusion inhibitor member 406. The diffusion inhibitor member 406 is configured to be disposed over a portion of a medical device 410 and coupled to a support member 408 of a packaging system. The diffusion inhibitor member 406 is configured as a polymeric film having an adhesive backing around a perimeter. The diffusion inhibitor member 406 is sized and shaped such that a catheter tip 413 and a sufficient length ($L_2$), for example at least one inch, of an elongate shaft 414 of the medical device 410 is covered by the diffusion inhibitor member 406 such that the infusion of VHP into the diffusion inhibitor member 406 is limited. The diffusion inhibitor member 406 may be formed into any suitable shape, such as a circle, square, triangle, rectangle, or any other polygonal shape.

In use, the packaging systems described herein, such as packing system 100 may be used to prevent exposure of medical devices to whole-room disinfecting gases and vapors such that degradation of the polymers used to form the medical devices is prevented. Using the packaging system of FIGS. 1-3C as an example, the medical device 110 may be manufactured according to acceptable techniques and coupled to the support member 108. The diffusion inhibitor member 106 may be disposed over the end of the support member 108 and over the distal end of the medical device 110 such that the diffusion inhibitor member 106 covers the catheter tip 113 and a portion of the shaft 114 of the medical device 110. In other embodiments, the diffusion inhibitor member 106 may be configured to cover other portions of the medical device 110. For example, in some embodiments, the diffusion inhibitor 106 may extend from a distal end of the medical device 110 along the entire shaft 114 of the medical device 110 and may extend such that it extends to, or extends over, the connector 115 of the medical device 110. In other words, the open end 117 of the diffusion inhibitor 106 may be disposed along any portion of the shaft 114 or along any portion of the connector 115. In some embodiments, the diffusion inhibitor may extend to, or beyond, the end of the support member 108. Regardless of the length of the diffusion inhibitor member 106, the diffusion inhibitor member 106 may have an open end 117. In some embodiments, the diffusion inhibitor member 106 is disposed over just the medical device 110. The medical device 110, the support member 108, and the diffusion inhibitor member 106 may be disposed into a primary package 120 through an open end. In some embodiments, the diffusion inhibitor member 106 may be disposed on the outside of the primary package such the diffusion inhibitor member is disposed over a portion of the medical device 110 inside the primary package. The open end of the primary package 120 may be sealed with heat and pressure or pressure forming the packaging system 100. In some embodiments, the packaging system 100 may be packaged in a secondary package system, such as a dispensing box or a shipping box.

Embodiments wherein the diffusion inhibitor 106 comprises a sealed pouch are likewise within the scope of this disclosure. For example, the diffusion inhibitor 106 may comprise a foil pouch that fully encloses the medical device 110.

The packaging system 100 may be exposed to a sterilizing gas, such as ethylene oxide, such that the medical device 110 is sterilized. The presence of the diffusion inhibitor 106 may allow for a sufficient amount of ethylene oxide to reach the portion of the medical device 110 covered by the diffusion inhibitor member 106 (such as catheter tip 113) such that the portion of the medical device 110 covered by the diffusion inhibitor member 106 is sterilized along with the other components of the system.

The packaging system 100 may then be shipped to a healthcare facility and placed in a clinical procedure room, such as an operating room, a diagnostic suite, a cath lab, etc. The clinical procedure room may be disinfected with a whole-room disinfecting gas or vapor, such as vaporized hydrogen peroxide (VHP), formaldehyde gas, or chlorine dioxide gas. The disinfecting gas or vapor may diffuse into the primary package 120. The diffusion inhibitor member 106 may prevent the disinfecting gas or vapor from contacting the portion of the medical device 110 covered by the diffusion inhibitor member 106. The packaging system 100 may prevent degradation of the polymer used to form the medical device 110 because the disinfecting gas or vapor is prevented or limited from diffusion into the cavity 107 of the diffusion inhibitor member 106 and contacting the medical device 110.

In other words, diffusion inhibitor member 106, 406 such as those described herein may be configured such that certain sterilizing agents, such as ethylene oxide gas are allowed to act on the covered portion of a medical device 110, 410 while certain whole-room disinfectants, such as VHP are prevented acting on the covered portion in such as way as to damage the covered portion. As discussed above, the diffusion inhibitor member 106, 406 may be configured with an open end (117 of FIG. 3A) while still inhibiting VHP from acting on the covered portion.

The effectiveness of the packaging system 100 of the present disclosure was tested. Direct evaluation of prevention of VHP contact with the surface of the medical device was not possible due to a lack of a residue left by VHP. Instead, polymeric degradation was measured following repeated exposure of the packaging system 100 comprising the diffusion inhibitor member 106 to VHP. The packaging system 100 was compared to a control packaging system without the diffusion inhibitor member 106. Samples of the packaging system 100 and the control packaging system were exposed to 10 cycles of VHP. The samples included groups oriented with the open end 117 of the diffusion inhibitor member 106 oriented upwards, downwards, and lying flat. Also, two different lengths of the diffusion inhibitor member 106 were tested. A short length covered the catheter tip 113 and one inch of the elongate shaft 114 of the medical device 110. A long length covered the catheter tip 113 and seven inches of the elongate shaft 114. To test for polymeric degradation, lengths of the catheter tips 113 were cut and tested for tensile strength.

Figure 5:
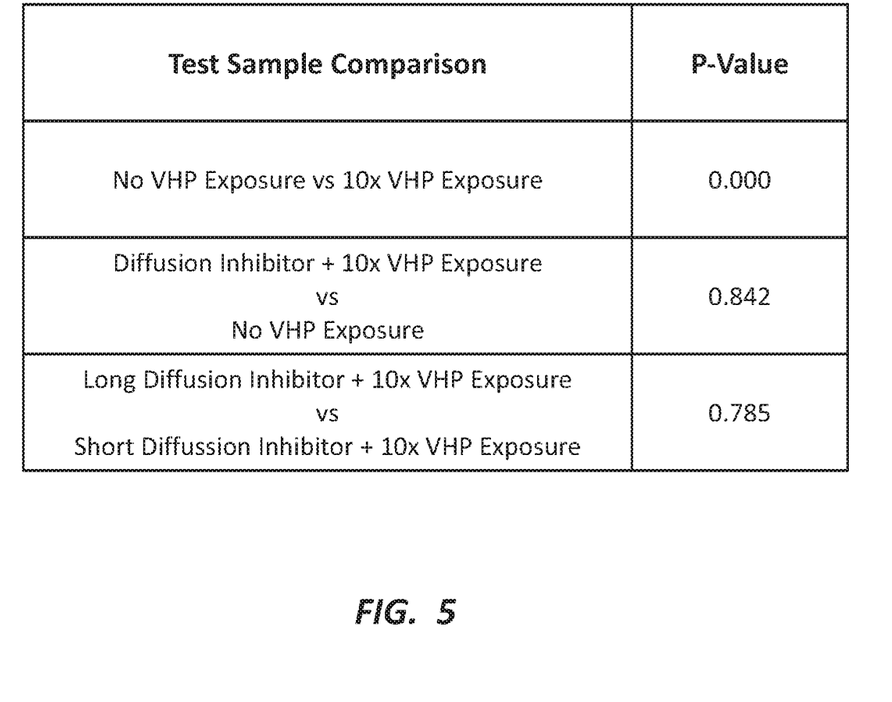
FIG. 5 depicts a table of test results.

FIG. 5 shows the test results. The results of the testing showed that exposure to VHP (without a diffusion inhibitor) significantly decreases the tensile strength of the material of the catheter tip 113 compared to the catheter tips 113 that were not exposed to VHP ($p=0.000$) where a p value of less than 0.05 shows a significant difference between compared samples. There was no significant difference between catheter tips exposed to VHP with diffusion inhibitors and catheter tips not exposed to VHP ($p=0.842$). The length of the diffusion inhibitor member 106 was found not to be critical as long as one inch of the elongate shaft 114 was covered ($p=0.785$). In summary, the test results indicate that the diffusion inhibitor member 106 of the packaging system 100 is effective at limiting the medical device 110 from exposure to VHP.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:
1. A medical device packaging system, comprising:
a primary package comprising:
a breathable first portion; and
a second portion coupled to the breathable first portion;
a diffusion inhibitor member disposed within the primary package, comprising an open-ended bag with a cavity, wherein the diffusion inhibitor member limits exposure of an elongate medical device to vaporized hydrogen peroxide, the elongate medical device comprising an elongate shaft and a catheter tip; and a support member disposed within the primary package, wherein the support member is coupled to the elongate medical device, wherein the catheter tip, at least one inch of the elongate shaft, and a distal end of the support member is disposed within the diffusion inhibitor.

2. The medical device packaging system of claim 1, wherein the diffusion inhibitor member comprises at least one material selected from the group consisting of: polyethylene, polypropylene, paper/polyethylene lamination, vinyl, and nylon.

3. The medical device packaging system of claim 1, wherein the diffusion inhibitor member comprises at least one wall having a thickness of from 0.002 inch to 0.003 inch.

4. The medical device packaging system of claim 1, wherein the diffusion inhibitor member comprises an adhesive backed film configured to cover the catheter tip and at least one inch of the elongate shaft.

5. The medical device packaging system of claim 1, wherein the diffusion inhibitor member is configured to conform to the shape of the catheter tip.

6. The medical device packaging system of claim 1, wherein the diffusion inhibitor member is configured to restrict diffusion of a whole-room disinfecting gas and/or vapor into the cavity and onto a surface of the elongate medical device.

7. The medical device packaging system of claim 6, wherein the diffusion inhibitor member permits gas sterilization of the catheter tip and a portion of the elongate shaft.

8. The medical device packaging system of claim 1, wherein the breathable first portion allows passage of ethylene oxide gas across the breathable first portion.

* * * * *